United States Patent [19]
Nizzola

[11] Patent Number: 5,314,422
[45] Date of Patent: May 24, 1994

[54] EQUIPMENT FOR THE CORRECTION OF PRESBYOPIA BY REMODELLING THE CORNEAL SURFACE BY MEANS OF PHOTO-ABLATION

[75] Inventor: Guido M. Nizzola, Modena, Italy

[73] Assignee: Nibatec S.A., Chiasso, Switzerland

[21] Appl. No.: 790,436

[22] Filed: Nov. 12, 1991

[30] Foreign Application Priority Data

Nov. 14, 1990 [IT] Italy ............................... 40147 A/90

[51] Int. Cl.$^5$ .............................................. A61N 5/06
[52] U.S. Cl. ........................................... 606/5; 606/17
[58] Field of Search ....................... 128/345, 347, 348; 606/4-6, 10-19

[56] References Cited

FOREIGN PATENT DOCUMENTS 296982 12/1988 European Pat. Off. ................ 606/5

*Primary Examiner*—David M. Shay
*Attorney, Agent, or Firm*—Darby & Darby

[57] ABSTRACT

The invention relates to equipment for the correction of presbyopia by means of corneal surface modelling by photo-ablation, of the type which uses a laser beam (16) (excimer laser) which is masked with a special mask (5) in such a way as to strike surfaces (19) of the cornea (3) in a sickle-shape configuration and located in proximity to the lower area of the pupil rim (20), on which surfaces (19) a removal action of very small-thickness uniform tissue layers is effected.

5 Claims, 2 Drawing Sheets

EQUIPMENT FOR THE CORRECTION OF PRESBYOPIA BY REMODELLING THE CORNEAL SURFACE BY MEANS OF PHOTO-ABLATION

BACKGROUND OF THE INVENTION

The invention relates to equipment for the correction of presbyopia by remodelling the corneal surface by means of photo-ablation. The prior art embraces the use of special laser equipment, that is, excimer lasers, able to generate a radiation beam capable of vaporising in an extremely regular and precise way very thin layers, of microscopic thickness (measured in um) of the eye cornea tissue. Such equipment is currently used for the remodelling of the corneal curvature to eliminate various refraction defects. To this end the prior art teaches the use of diaphragms and masks which have the task of permitting the laser beam to reach and ablate the corneal surface in pre-established areas. By the use of masks and diaphragms, whose apertures can be controlled and co-ordinated with programmed laser beam application times, it is possible to realise a kind of step-shaped "sculpting" of the cornea through a succession of photo-ablated excisions of uniform single-layers, of differing lengths, from the cornea itself.

SUMMARY OF THE INVENTION

The principal aim of the present invention is the perfection of a device which, by exploiting the above-described technology, permits of realising an effective correction of presbyopia.

The invention, as described in the claims which follow, solves the problem by proposing the use, in conjunction with an excimer laser, of a template or shaped mask so equipped as to permit of a special modelling by photo-ablation of a part of the cornea surface situated close to the lower part of the pupil rim.

An advantage of the invention is its substantial simplicity.

BRIEF DESCRIPTION OF THE DRAWINGS

Further characteristics and details will better emerge from the detailed description which follows, of a preferred but not exclusive embodiment of the invention, here illustrated purely in the form of a non-limiting example in the enclosed drawings, in which.

DESCRIPTION OF THE PREFERRED EMBODIMENTS

Figure 1:
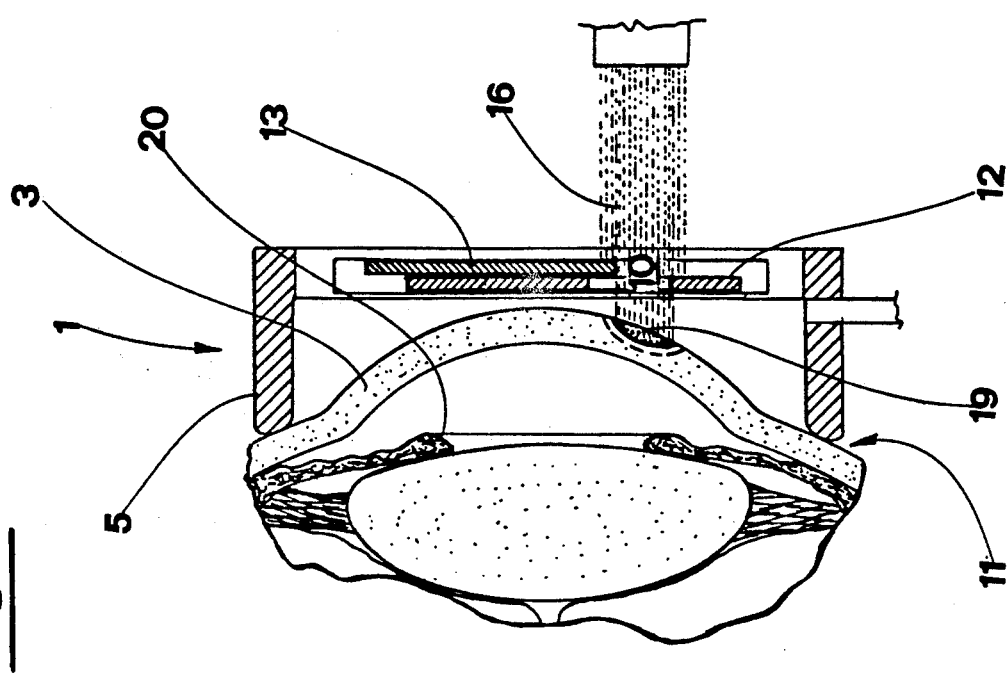
FIG. 1 shows a schematic section along plane II—II of the following FIG. 2.
Figure 2:
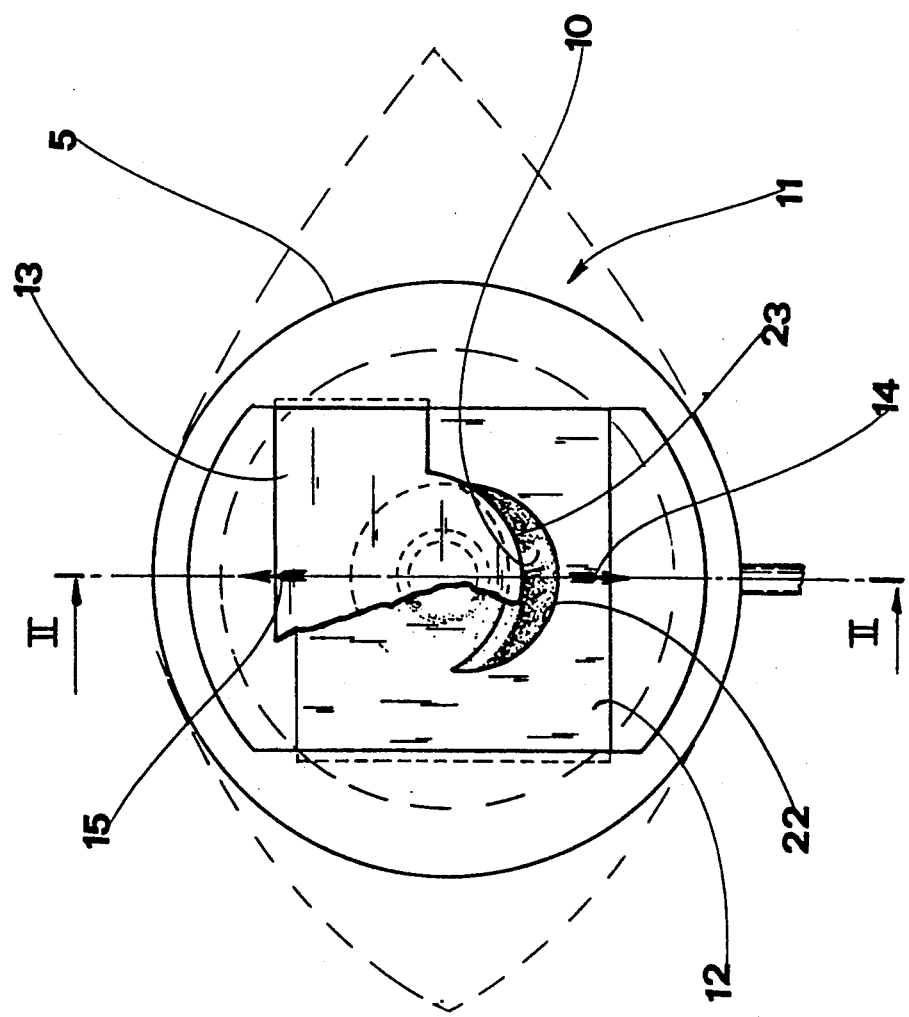
FIG. 2 shows a right-side schematic view of FIG. 1.

With reference to the drawings, 1 indicates a diaphragm, or mask applied to an eyeball 11. The mask 1 comprises a structure having the function of a frame 5, envisaged to permit of leaning directly on the eyeball 11, on which frame 5 an organ with mask function 1 is envisaged comprising two flat plates 12 and 13 arranged one above the other and guided to slide along the same plane, but in opposite directions with respect to the frame 5. The two plates 12 and 13 are therefore reciprocally constrained by a mechanism by means of which their contemporaneous symmetrical movement with respect to the frame 5 is produced according to the directions indicated (and vice-versa) by the two arrows 14 and 15. In particular, the first plate 12 is partially shaped with a slit in the form of a circumferential arc, said slit edge being destined to define the rim or curved edge 22 of the aperture 10 of the mask 1. The plate 13 has instead a convex shaping in the form of a circumferential arc, which arc rim defines the rim or edge 23 of the said aperture 10. In particular, the radius of the curved edge 23 is greater than the curvature radius of the curved edge 22 so that the aperture 10 in any intermediate position assumed by the two plates 12 and 13, has a sickle-shape configuration.

The diameters of the two circumferential arcs constituting the edges 22 and 23 are determined in such a way as to be similar to the diameter of the pupil opening.

Figure 3:
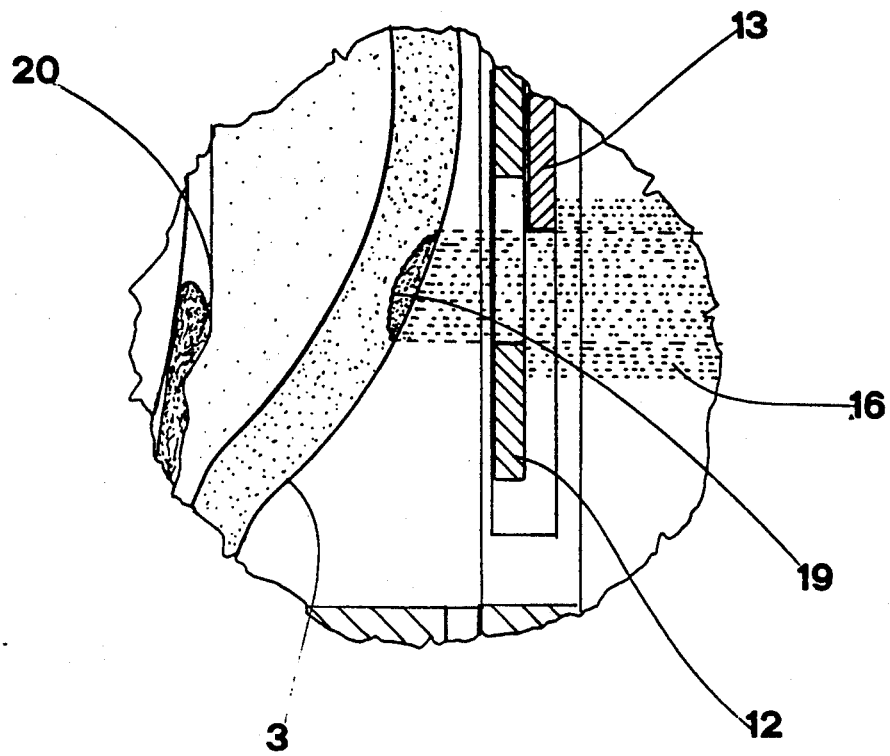
FIGS. 3 and 4 show, in enlarged and altered scale, a part of FIG. 1 represented in two different operative configurations.
Figure 4:
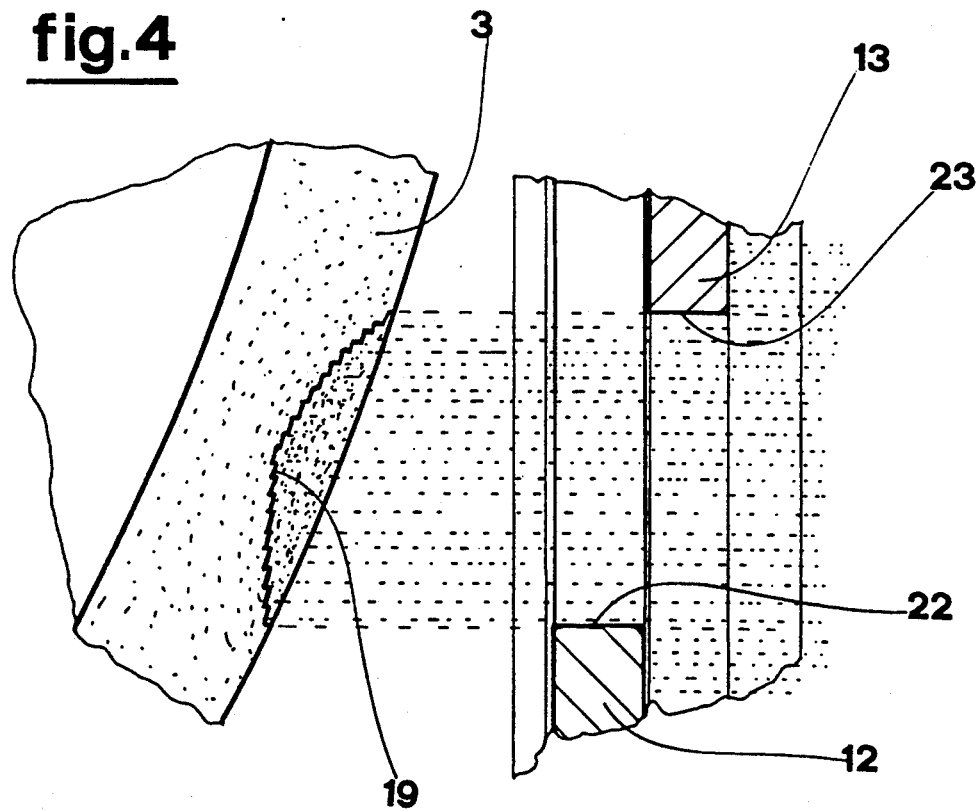

The mask 1 is arranged so as to direct, through its aperture 10, a laser beam 16 on an area 19 of the corneal surface 3, which area 13 is situated in proximity to the lower part of the pupil rim 20. The operation is performed according to a succession of operative phases which initially envisage that the two plates, 12 and 13, should be reciprocally positioned at the minimum distance so as to identify the minimum value of the aperture 10. Subsequently, a progressive reciprocal distancing between the two plates 12 and 13, activated with a pre-established sequence of tiny relative movements according to the two arrows 14 and 15, is performed up until the maximum value of the said aperture 10 is reached. The laser beam 16, produced by an excimer laser, is synchronised with the pre-established values of the aperture 10. With every different value of the said aperture 10, the laser beam 16 strikes a pre-established surface of the cornea which surface, in the example, comprises internally the surface defined by the preceding aperture 10 value. Some phases of the entire sequence are schematically represented in FIGS. 3 and 4, in which the step-like modelling of the corneal areas involved in the laser beam 16 action is shown. At the end of the operation, the area of the cornea near the lower rim of the pupil, indicated in the figure with the number 19, has been remodelled with a sort of shaped recess, which is more or less accentuated depending on the degree of defect correction required. The remodelled area thus constitutes a zone of the cornea which functions differently from the rest of said cornea, like in fact a lens with a different focal length which focal length permits of focussing on near objects. The particular conformation of the corneal area 19, as well as its positioning on the lower pupil rim 20, permit, in the case of presbyopia, of a notable improvement in near sight without however disturbing longsight ability. With the aim of minimising the longsight disturbance, the area 19 and thus the shaping of the aperture 10 is proportioned to the diameter of the pupil and in particular the edge 23 of the plate 13 whose diameter is about the same as that of the pupil rim 20. Thanks to the symmetry of the movement of the two plates 12 and 13 and to the positioning of the aperture 10 with respect to the pupil, the sickle-shaped recess realised on the corneal surface has its deepest point at about the level of the pupil rim 20. For the correct functioning of the entire operation, the mask 1 is equipped with a suction system arranged in the lower part of the frame 5, that is, immediately below the two plates 12 and 13.

What is claimed:

1. Equipment for the correction of presbyopia by shaping of a corneal surface at a pupil of an eye using an output of laser energy, said pupil having a periphery having a curvature, said laser output being capable of removing a thin layer of tissue from said corneal surface when pulsed, said equipment comprising:

- a mask interposed between said laser output and said corneal surface, said mask having an aperture for allowing said laser output to pass therethrough, said aperture having a curved edge, said curved edge having a curvature substantially similar to said curvature of said pupil;
- a frame for supporting said mask above said corneal surface;
- said mask having two mask elements slidably mounted within said mask, each of said mask elements having a curved edge, said two mask elements positioned within said mask such that said aperture is blocked by said mask elements except at an aperture portion defined by said two curved edges when in a facing arrangement, a first of said curved edges being convex, a second of said curved edges being concave, said mask elements being slidable to vary the dimensions of said aperture portion.

2. Equipment as in claim 1, wherein said frame further comprises a means for contacting said eye away from said pupil.

3. Equipment as in claim 1, wherein said first of said curved edges has a curvature greater than that of said second of said curved edges.

4. Equipment as in claim 3, wherein said curved edges are circumferential arcs.

5. Equipment as in claim 4, wherein said mask elements are comprised of two flat plates mounted in said frame such that they may slide one on top of another in parallel, but in opposite directions to one another; one of said plates being formed with a slit in the form of a crescent having an inner and an outer arc, said outer arc is formed by said second curved edge;

the other of said plates having a convexly curved edge defining said first curved edge.

* * * * *